(12) United States Patent
DiDomenico et al.

(10) Patent No.: US 9,351,773 B2
(45) Date of Patent: May 31, 2016

(54) COMPRESSOR-DISTRACTOR

(71) Applicant: DePuy Synthes Products, LLC, Raynham, MA (US)

(72) Inventors: Scott R. DiDomenico, Warrington, PA (US); Jason S. Chan, Dresher, PA (US); Jeff W. Mast, Reno, NV (US); Keith A. Mayo, Gig Harbor, WA (US); Brett B. Bolhofner, St. Petersburg, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/272,483

(22) Filed: May 7, 2014

(65) Prior Publication Data
US 2014/0243903 A1    Aug. 28, 2014

Related U.S. Application Data

(63) Continuation of application No. 10/884,704, filed on Jul. 2, 2004, now Pat. No. 8,753,348.

(51) Int. Cl.
*A61B 17/80* (2006.01)

(52) U.S. Cl.
CPC .......... *A61B 17/8004* (2013.01); *A61B 17/8019* (2013.01)

(58) Field of Classification Search
CPC .................. A61B 17/8004; A61B 17/8019
USPC ......... 606/101, 205–208, 246, 279–281, 291, 606/86 B
See application file for complete search history.

(56) References Cited

U.S. PATENT DOCUMENTS

| | | |
|---|---|---|
| 2,002,021 A | 5/1935 | Rouse |
| 2,631,585 A | 3/1953 | Siebrandt |
| 2,850,803 A | 9/1958 | Briskman et al. |
| 3,386,437 A | 6/1968 | Treace |
| 3,400,711 A | 9/1968 | Huz et al. |
| 3,709,219 A | 1/1973 | Halloran |
| 3,750,652 A | 8/1973 | Sherwin |
| 3,840,014 A | 10/1974 | Ling et al. |
| 3,866,607 A | 2/1975 | Forsythe et al. |
| 3,960,147 A | 6/1976 | Murray |
| 4,050,464 A | 9/1977 | Hall |

(Continued)

FOREIGN PATENT DOCUMENTS

| | | |
|---|---|---|
| CH | 394479 A | 6/1965 |
| CH | 655646 A5 | 5/1986 |

(Continued)

*Primary Examiner* — Jerry Cumberledge
*Assistant Examiner* — David C Comstock
(74) *Attorney, Agent, or Firm* — Fay Kaplun & Marcin, LLP

(57) ABSTRACT

A tool is disclosed for use in distracting and compressing fractures of any of a variety of bones. In particular, the tool has a pair of engaging arms, one arm having a hook element to engage a bone plate connected to one side of a fracture, and the other arm having at least one recess for engaging a head of a bone screw or guide wire connected to the other side of the fracture. Actuation of the tool causes the opposing bone segments of the fracture to be pushed apart or drawn together, depending on whether the tool handles are squeezed together or pulled apart. The tool may have a scissors joint that allows the ends of the tool to maintain a parallel alignment during operation, thus reducing the chances for misalignment of the bone segments during operation.

21 Claims, 7 Drawing Sheets

(56) References Cited

U.S. PATENT DOCUMENTS

| | | | |
|---|---|---|---|
| 4,066,082 A | 1/1978 | Arcan et al. |
| 4,102,339 A | 7/1978 | Weber et al. |
| 4,271,836 A | 6/1981 | Bacal et al. |
| 4,475,544 A | 10/1984 | Reis |
| 4,502,475 A | 3/1985 | Weigle et al. |
| 4,554,848 A | 11/1985 | Galletto |
| D291,729 S | 9/1987 | Greig |
| 4,898,161 A | 2/1990 | Grundei |
| 4,929,247 A | 5/1990 | Rayhack |
| 4,997,432 A | 3/1991 | Keller |
| 5,108,395 A | 4/1992 | Laurain |
| 5,122,130 A | 6/1992 | Keller |
| 5,147,358 A | 9/1992 | Remmler |
| 5,154,721 A | 10/1992 | Perez |
| 5,297,538 A | 3/1994 | Daniel |
| 5,423,826 A | 6/1995 | Coates et al. |
| 5,431,653 A | 7/1995 | Callaway |
| 5,484,447 A | 1/1996 | Waldock et al. |
| 5,611,519 A | 3/1997 | Garcia |
| D381,746 S | 7/1997 | Koros et al. |
| 5,672,175 A | 9/1997 | Martin |
| 5,704,937 A | 1/1998 | Martin |
| 5,797,910 A | 8/1998 | Martin |
| 5,797,919 A | 8/1998 | Brinson |
| D401,335 S | 11/1998 | Koros et al. |
| 5,849,012 A | 12/1998 | Abboudi |
| 5,885,210 A | 3/1999 | Cox |
| 5,997,545 A | 12/1999 | Doherty et al. |
| 6,007,535 A | 12/1999 | Rayhack et al. |
| 6,007,538 A | 12/1999 | Levin |
| 6,017,342 A | 1/2000 | Rinner |
| 6,080,162 A | 6/2000 | Dye et al. |
| 6,193,721 B1 | 2/2001 | Michelson |
| 6,200,318 B1 | 3/2001 | Har-Shai et al. |
| 6,261,296 B1 | 7/2001 | Aebi et al. |
| 6,287,307 B1 | 9/2001 | Abboudi |
| 6,332,887 B1 | 12/2001 | Knox |
| 6,398,783 B1 | 6/2002 | Michelson |
| 6,416,528 B1 | 7/2002 | Michelson |
| 6,428,542 B1 | 8/2002 | Michelson |
| 6,432,106 B1 | 8/2002 | Fraser |
| 6,454,771 B1 | 9/2002 | Michelson |
| 6,527,776 B1 | 3/2003 | Michelson |
| 6,533,786 B1 | 3/2003 | Needham et al. |
| 6,551,316 B1 * | 4/2003 | Rinner et al. ............... 606/57 |
| 6,558,392 B1 | 5/2003 | Martini |
| 6,565,568 B1 | 5/2003 | Rogozinski |
| 6,565,570 B2 | 5/2003 | Sterett et al. |
| 6,592,586 B1 | 7/2003 | Michelson |
| 6,599,294 B2 | 7/2003 | Fuss et al. |
| 6,616,666 B1 | 9/2003 | Michelson |
| 6,620,163 B1 | 9/2003 | Michelson |
| 6,648,891 B2 | 11/2003 | Kim |
| 6,692,503 B2 | 2/2004 | Foley et al. |
| 6,712,825 B2 | 3/2004 | Aebi et al. |
| 6,716,218 B2 | 4/2004 | Holmes et al. |
| 6,739,068 B1 * | 5/2004 | Rinner ............... 33/783 |
| 6,740,087 B2 | 5/2004 | Knox |
| 6,746,449 B2 | 6/2004 | Jones et al. |
| 7,189,234 B2 * | 3/2007 | Zucherman et al. ......... 606/249 |
| 2001/0029377 A1 | 10/2001 | Aebi et al. |
| 2002/0120273 A1 | 8/2002 | Needham et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0040746 A1 | 2/2003 | Mitchell et al. |
| 2003/0045880 A1 | 3/2003 | Michelson |
| 2003/0060828 A1 | 3/2003 | Michelson |
| 2003/0125739 A1 | 7/2003 | Bagga et al. |
| 2003/0181912 A1 | 9/2003 | Michelson |
| 2003/0187453 A1 | 10/2003 | Schlapfer et al. |
| 2003/0191471 A1 | 10/2003 | Michelson |
| 2003/0191472 A1 | 10/2003 | Michelson |
| 2004/0024411 A1 | 2/2004 | Newton |
| 2004/0039397 A1 | 2/2004 | Weber |
| 2005/0165486 A1 | 7/2005 | Trieu |

FOREIGN PATENT DOCUMENTS

| | | |
|---|---|---|
| CN | 100542496 C | 9/2009 |
| CN | 101653371 A | 2/2010 |
| DE | 1880848 U | 10/1963 |
| DE | 19828137 A1 | 1/2000 |
| DE | 19914387 A1 | 10/2000 |
| GB | 1118773 A | 7/1968 |
| GB | 2198647 A | 6/1988 |
| WO | 9834553 A1 | 8/1998 |
| WO | 0101874 A1 | 1/2001 |
| WO | 2006014384 A2 | 2/2006 |

* cited by examiner

COMPRESSOR-DISTRACTOR

PRIORITY CLAIM

The present application is a Continuation Application of the U.S. patent application Ser. No. 10/884,704 filed on Jul. 2, 2004, now U.S. Pat. No. 8,753,348. The disclosures of the above-identified patent(s)/application(s) are incorporated herein by references.

FIELD OF THE INVENTION

The present invention relates to a hand-held tool for moving bone segments with respect to each other, such as for example, for arranging a pair of opposing bone segments to be connected with a bone plate. More particularly, the invention relates to a tool used first to distract fractured bone segments so they may be properly aligned, and then to compress the aligned segments together so they may be fixed together with an orthopedic bone plate.

BACKGROUND OF THE INVENTION

The use of bone plates for stabilizing fractured bones is widely accepted. The plates are used by surgeons to stabilize, mend, or align a patient's bones as well as alter compression of patient's bones, and are typically fastened to the bones with a plurality of fasteners, such as screws that are installed through holes in the plate.

Prior to fixation of a fracture the surgeon typically may manipulate the bone segments to return them to proper orientation and alignment. To accomplish this, the surgeon may first apply a distraction or separation force to the bone segments, which may cause the surrounding soft tissue to urge the bone segments back toward their general pre-fracture position. The bone segments may then be individually manipulated to achieve a more precise alignment, followed by the application of a compression force to the segments to press them together to increase the likelihood that the bone segments will fuse.

Thus, there is a need for an instrument that may be used to apply a distraction or compression force to fractured bones to aid in their alignment and subsequent re-engagement.

SUMMARY OF THE INVENTION

A tool may be provided for manipulating bone segments, the tool may comprise an actuating end may have first and second handles pivotably coupled together and an engaging end may have first and second engaging arms. The first engaging arm may have a first end coupled to the first handle and a second end configured to receive at least a portion of a bone fastener. The second engaging arm may have a first end coupled to the second handle and a second end configured to engage a bone plate. The second end of the first engaging arm further may have at least a first lateral side surface may have a first recess configured to receive at least a portion of the bone fastener.

The bone fastener may be a bone screw, and the first recess may be configured to receive a head portion of the bone screw. The first recess may have a depth of from about 0.1 mm to about 3.0 mm. Alternatively, the bone fastener may comprise a surgical guide wire, wherein the second end of the first engaging arm may comprise a second recess configured to receive at least a portion of the guide wire. The second recess may have a depth of from about 0.1 mm to about 1.8 mm. Further, the first and second recesses may be at least partially coextensive.

The second end of the second engaging arm may comprise a hook configured to engage the bone plate. The hook may further be configured to engage the end surface of the bone plate or a bone screw hole of the bone plate.

The bone fastener may be a surgical guide wire, wherein the second lateral side surface has a second recess configured to receive at least a portion of the guide wire.

The second end of the first engaging arm further may have at least a second lateral side surface may have a first recess configured to receive at least a portion of the bone fastener. The bone fastener may be a bone screw, and the first recess of the second lateral side surface may be configured to receive a head portion of the bone screw.

Each of the first and second handles may be coupled to one of the first and second engaging arms such that moving the first and second handles together moves the first and second engaging arms with respect to each other. The first and second engaging arms may be pivotably coupled to the first and second handles, respectively.

A scissor-joint may be disposed between the first and second engaging arms. The scissor-joint may be operable to maintain the arms oriented substantially parallel with respect to each other when the first and second handles are moved. The tool further may be configured such that moving the first and second handles together results in the first and second engaging arms moving apart.

A system is provided for manipulating first and second fractured bone segments. The system may comprise a tool comprising an actuating end with first and second handles pivotably coupled together and an engaging end having first and second engaging arms. The first engaging arm may have a first end coupled to the first handle and a second end having a first recess configured to receive at least a portion of a bone fastener therein. The second engaging arm may have a first end coupled to the second handle and a second end configured to engage a bone plate. At least one bone fastener and a bone plate may also be provided.

Thus, when the bone fastener is engaged with the first bone segment and the bone plate is engaged with the second bone segment, the first and second engaging arms are engageable with the fastener and plate such that moving the first and second handles with respect to each other moves the first and second bone segments with respect to each other.

The bone fastener may be a bone screw, and the first recess may be configured to receive a head portion of the bone screw. The first recess may have a depth of from about 0.1 mm to about 3.0 mm. The bone fastener may comprise a surgical guide wire, and the second end of the first engaging arm may have a second recess configured to receive at least a portion of a surgical guide wire.

The second recess may have a depth of from about 0.1 mm to about 1.8 mm. The first and second recesses further may be at least partially coextensive. The second end of the second engaging arm may be a hook configured to engage the bone plate.

The hook may be configured to engage at least one of an end surface of the bone plate and a bone screw hole of the bone plate. The first engaging arm further may have a first lateral side surface and the first recess may be disposed within the first lateral side surface and configured to receive at least a portion of the bone fastener, which may be a bone screw.

The first engaging arm further may have a second lateral side surface with a first recess configured to receive at least a portion of the bone fastener. The bone fastener may comprise a bone screw, and the first recesses of the first and second lateral side surfaces may be configured to receive the head of the screw.

The bone fastener may comprise a surgical guide wire, wherein the first and second lateral side surfaces each have a second recess configured to receive at least a portion of a surgical guide wire.

Each of the first and second handles may be coupled to one of the first and second engaging arms such that moving the first and second handles together results in movement of the first and second engaging arms with respect to each other. The first and second engaging arms may be pivotably coupled to the first and second handles, respectively.

The tool may further comprise a scissor-joint disposed between the first and second engaging arms. The scissor-joint may be operable to maintain the arms oriented substantially parallel with respect to each other when the first and second handles are moved. The tool further may be configured so that moving the first and second handles together results in the first and second engaging arms moving apart.

A method of moving at least first and second fractured bone segments of patient with respect to each other is also provided, the method comprising the steps of: (a) providing a tool may have an actuating end with first and second handles pivotably coupled together; the tool further having an engaging end with first and second engaging arms, the first engaging arm having a first end coupled to the first handle and a second end configured to receive at least a portion of a bone fastener, the second engaging arm having a first end coupled to the second handle and a second end configured to engage a bone plate; wherein the first engaging arm further has at least a first lateral side surface having a first recess configured to receive at least a portion of the bone fastener; (b) advancing the engaging end of the tool through an incisions in the patient's skin; (c) engaging a first bone fastener with the first bone segment; (d) engaging a bone plate with the second bone segment; (e) engaging the bone fastener with the first recess of the first engaging arm; (f) engaging the bone plate with the second engaging arm; and (g) moving the first and second handles with respect to each other to move the first and second bone segments with respect to each other.

The first bone fastener may be a bone screw, and the first recess may be configured to receive a head portion of the bone screw. Further, the first recess may have a depth of from about 0.1 mm to about 3.0 mm. Alternatively, the first bone fastener may comprise a surgical guide wire, and the first engaging arm further may comprise a second recess configured to receive at least a portion of the guide wire. The second recess may have a depth of from about 0.1 mm to about 1.8 mm. The first and second recesses may be at least partially coextensive.

The method may comprise additional step (g) which comprises moving the first and second handles away from each other such that the first and second engaging arms move away from each other, thereby moving the first and second bone segments away from each other.

The method may further comprise the steps of: (h) disengaging the first engaging arm from the first bone fastener; (d) disengaging the second engaging arm from the bone plate; (e) engaging the bone fastener with the second recess of the first engaging arm; (f) engaging the bone plate with the second engaging arm; and (g) moving the first and second handles apart to thereby move the first and second bone segments together.

Step (f) may comprise engaging a hook on the second engaging arm with a bone screw hole of the bone plate. The bone fastener may further be a bone screw, and the first recess of the second lateral side surface may be configured to receive a head portion of the bone screw. Alternatively, the bone fastener may comprise a surgical guide wire.

The first and second engaging arms may be pivotably coupled to the first and second handles, respectively. The tool may further comprise a scissor-joint disposed between the first and second engaging arms, the scissor-joint operable to maintain the arms oriented substantially parallel with respect to each other when the first and second handles are moved.

BRIEF DESCRIPTION OF THE DRAWINGS

For a better understanding of the nature and objects of the invention, reference should be made to the following detailed description, taken in conjunction with the accompanying drawings which show preferred features of the invention, in which like reference numerals refer to corresponding parts throughout the several views of the drawings and wherein.

DETAILED DESCRIPTION OF THE INVENTION

Figure 1:
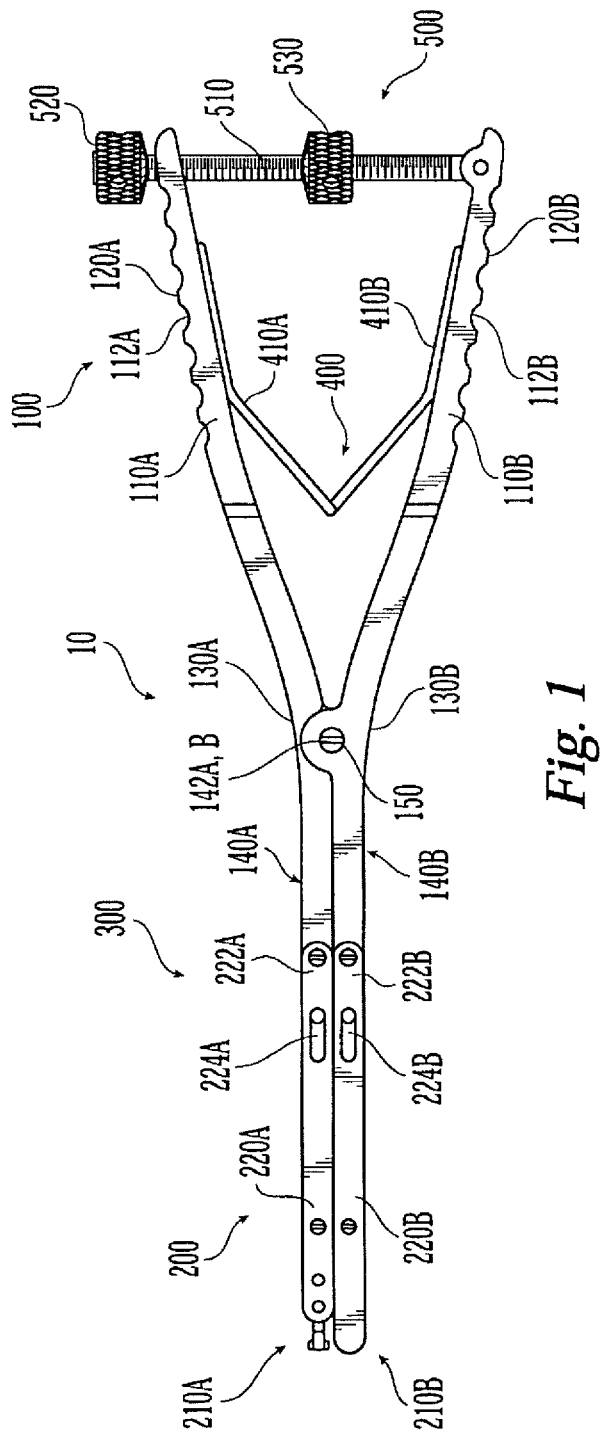
FIG. 1 is a side elevation view of a tool according to one embodiment of the present invention, with the tool shown in the closed position.
Figure 2:
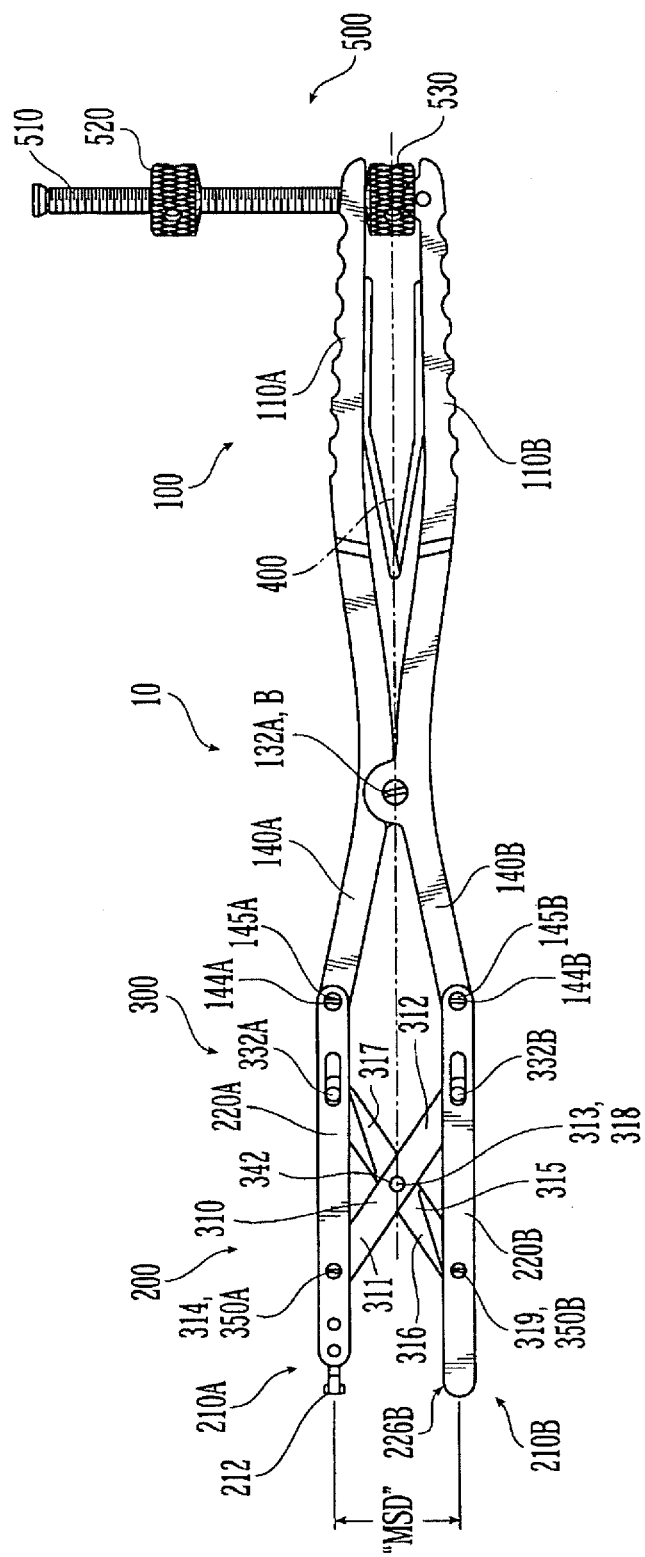
FIG. 2 shows a side elevation view of the tool of FIG. 1, with the tool being shown in the open position.
Figure 3:
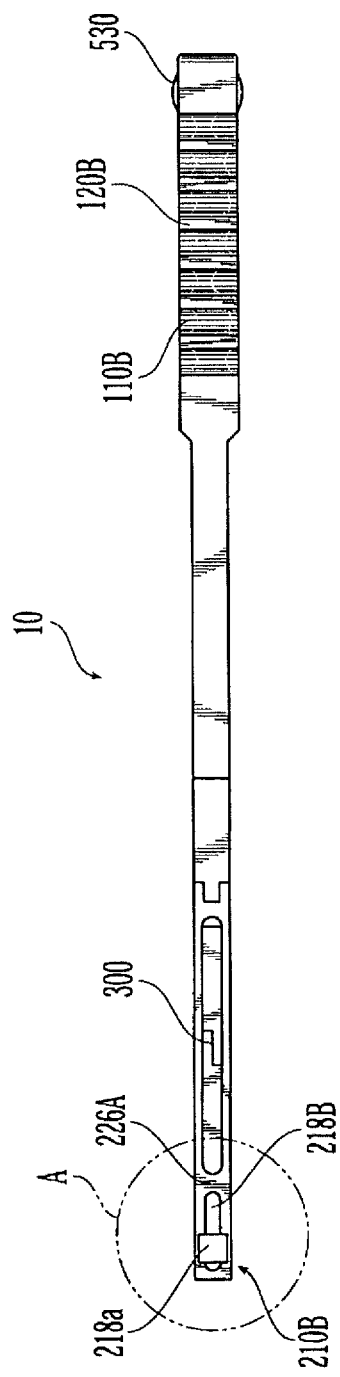
FIG. 3 is a top view of the tool of FIG. 1.

Referring to FIG. 1, there is shown an exemplary tool 10 adapted for distracting or compressing a pair of opposing fractured bone segments. The tool 10 may engage an orthopedic fixation element, such as a bone plate 1000 (FIG. 5A) or bone screw 1100, that is connected to one of the pair of segments. The tool 10 may be a generally pliers-like device having an actuating end 100 and a fixation-element engaging end 200. The actuating end 100 may comprise a pair of opposed handles 110A, B coupled at pivot portions 130A, B. The fixation-element engaging end 200 may comprise a pair of engaging arms 220A, B, each having a distal engaging end 210A, B configured to engage a separate orthopedic fixation element such as a bone plate, bone screw or guide wire (see FIGS. 5A-5C). Engaging arms 220A, B may further each have a proximal end 222A, B pivotably associated with a respective distal end 140A, B of handles 110A, B so that when the handles are squeezed together, the engaging ends 210A, B spread apart (FIG. 2). Thus, when the engaging ends 210A, B are engaged with bone plate 1000 and bone screw 1100 that themselves are each fixed to a respective fractured bone segment 2000, 2100, (FIGS. 5A-5C), squeezing the handles 110A, B together may cause the bone segments to spread apart. Conversely, spreading the handles 110A, B may draw the bone segments together. A biasing assembly 400 may be provided to urge the handles 110A, B apart, and a locking assembly 500 may be provided to allow the user to lock the device in a selected position.

Handles 110A, 110B may each have a proximal gripping portion 120A, B, a distal engaging-arm engaging portion 140A, B, and an intermediate pivot portion 130A, B. The gripping portions may have ribs 112A, 112B to facilitate gripping by the user. The pivot portions 130A, B may have a transverse hole 142A, B for receiving a fastener 150 such as a pin, screw, rivet, etc. therethrough to allow the handles to pivot with respect to each other. Likewise, the engaging-arm engaging portions 140A, B may each have a similar transverse hole 144A, B, for receiving a similar fastener 145A, B to pivotally engage the proximal end 222A, B of a respective engaging arm 220A, B.

The engaging arms 220A, B may be connected together via a scissors assembly 300 that operates to maintain the arms 220A, B substantially parallel with respect to each other as they are opened and closed. This parallel arrangement causes the engaging ends 210A, B to remain in constant alignment with the associated fixation element 1000, 1100 throughout the full range of motion of the instrument 10, thus enhancing the engagement between the instrument 10 and the fixation elements 1000, 1100, 1200. This arrangement also may allow the user to apply distraction or compression motion that is substantially parallel to the longitudinal axis of the fractured bone, thus eliminating a potential source of bone segment misalignment in use.

Thus, scissors assembly 300 may comprise first and second scissor arms 310, 315 each having a first end 311, 316 and a second end 312, 317 and an intermediate pivot portion 313, 318. The first ends 311, 316 each have a transverse hole 314, 319 for receiving a pin 350A, B to pivotably connect the first ends 311, 316 to the first and second engaging arms 220A, B, The second ends 312, 317 each have a transversely projecting pin 332A, B configured to slide within a longitudinal slot 224A, B formed in the first and second engaging arms 220A, B. The intermediate pivot portions 313, 318 each has a transverse hole for receiving a pivot pin 342, to allow the arms 310, 315 to pivot with respect to each other. Thus arranged, when the instrument 10 is in the closed position illustrated in FIG. 1, the scissors assembly 300 assumes a folded position in which transversely projecting pins 332A, B are positioned adjacent the proximal end of longitudinal slots 224A, B. When the handles 110A, B are squeezed together, an opening movement is applied to the engaging arms 220A, B via fasteners 145A, B, which causes the scissors assembly 300 to open, forcing projecting pins 332A, B to slide distally within the associated longitudinal slots 224A, B. This opening movement may continue until the handles are brought fully together or until the pins 332A, B reach the distal ends of their associated slots 224A, B, as illustrated in FIG. 2.

The instrument 10 may be sized and configured to provide any of a range of distraction or compression length. Thus, as illustrated in FIG. 2, the engaging arms 220*a, b* may have a fully open position in which the arms are separated by a maximum separation distance "msd," as measured between the centerlines of the arms. In one embodiment of the instrument 10 for use with smaller bones such as the radius, ulna, tibia, etc., the maximum separation distance "msd" may be about 30 mm. In an alternative embodiment of the instrument 10, for use with larger bones such as the femur, the maximum separation distance may be about 60 mm. As will be apparent to one of ordinary skill in the art, the instrument may be scaled to provide any appropriate separation distance, depending on the application for which the instrument is intended.

It is noted that although the handles 110A, B, engaging arms 220A, B, and scissor mechanism 300 of the instrument 10 may all be illustrated as lying in the same plane, in order to facilitate visualization of the treatment site during distraction and compression, at least a portion of the handles 110A, B may be angled away from the plane of the engaging arms 220A, B.

Likewise, the handles 110A, B may be divergently flared or curved away from each other, and the length of slots 224A, B increased, to allow the engaging ends 210A, B to have a greater length of travel, thus increasing the maximum distance "mod" between the ends in the fully open position of FIG. 2. It will be apparent that the instrument may be provided with any appropriate combination of slot lengths and handle configurations to result in a desired maximum separation distance "mod."

As previously noted, a locking mechanism 500 may be provided adjacent to or within the engaging end 100 to maintain a desired distraction or compression position of the instrument 10. The locking mechanism 500 may include a spindle or threaded bolt 510 mounted on the second handle 110B and passing through the first handle 110A. A first internally threaded speed nut 520 may rotatably mounted on the threaded bolt 510 such that movement of the speed nut 510 along the bolt selectively inhibits movement of the first handle 110B away from the second handle 110A and thus maintains the bone portions in the desired distracted position. A second speed nut 530 may also be rotatably mounted on the threaded bolt 510 between the first and second handles 110A, B such that movement of the second speed nut 530 along the bolt selectively inhibits movement of the first handle toward the second handle 110A and thus maintains the bone portions in the desired compressed position.

A biasing element 400, such as a pair of leaf springs 410A, B, may further be provided to maintain handles 110A, B in a "neutral" spaced apart configuration such that engaging ends 210A, B are in the closed position of FIG. 1, ready for insertion through a small incision in the patient. Locking mechanism 500 may counteract biasing element 400 as desired.

The instrument 10 may also be provided with a dynamometer or force gauge (not shown) disposed between handles 110A, B to allow the surgeon to precisely determine the amount of force being applied to the bone segments using the instrument 10. This may be important, for example, in determining whether sufficient compressive force is being applied between the ends of the fractured bones to ensure proper healing, or to ensure that too much force is not being applied to the bone segments.

Figure 4A:
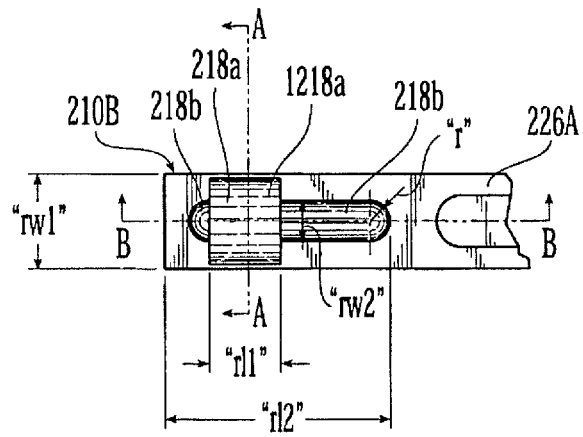
FIG. 4A is a detail view of the fixation-element engaging end of the tool of FIG. 1.
Figure 4B:
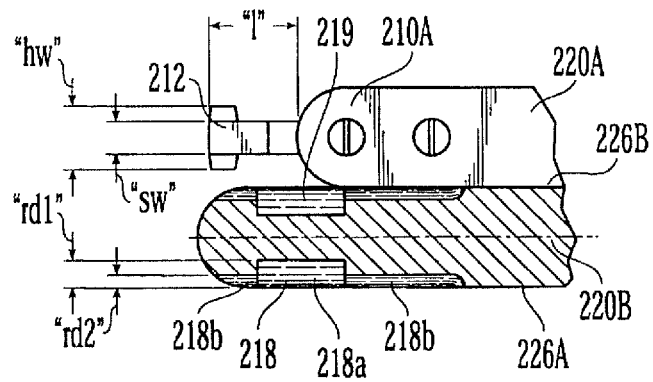
FIG. 4B is a side partial section view of the fixation-element engaging end of the tool of FIG. 1, taken along line B-B of FIG. 4A.
Figure 4C:
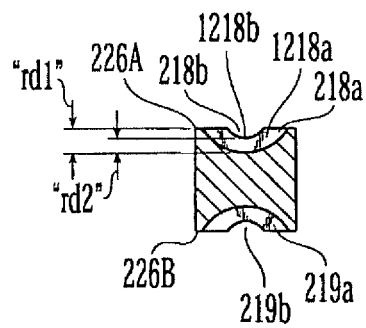
FIG. 4C is an end section view of one of the fixation-element engaging ends of the tool of FIG. 1, taken along line C-C of FIG. 4B.

Referring now to FIGS. 4A-4C, the engaging ends 210A, B of the instrument 10 will be described in greater detail. As shown in FIGS. 4A-4C, the engaging end 210A may comprise a hook element 212 configured to engage the end surface 1002 or the bone screw hole 1004, or articulated tension device hole 1005 (FIG. 5E), of a bone plate 1000 (FIG. 5A), while engaging end 21013 may have a pair of recesses 218, 219 configured to receive a head portion 1102 of a bone screw 1100 (FIGS. 5A-C) or a section of a surgical guidewire 1200 (FIG. 5D). This arrangement allows the device to be used to apply a force between first and second bone segments, where the first bone segment is connected to a bone plate and the second bone segment is connected to either a bone screw or guide wire.

As shown in greater detail in FIG. 4B, hook element 212 may be associated with the distal end 210A of engaging arm 220A. Specifically, hook element 212 may be connected to, and may extend distally from, the distal end 210A of engaging arm 220A. Hook 212 may have a longitudinally extending shank portion 214 with a transversely extending hook portion 216 disposed at a distal end thereof. The shank portion 214 may have a proximal end connected to the distal end of the engaging arm 220A. In the illustrated embodiment, the shank 214 is connected to the engaging arm 220A via a pair of machine screws 217, 218. Although any appropriate fastener or fastening method may be employed for this connection (the hook could even be made an integral part of the engaging arm 220A), screws provide the advantage of allowing the hook element 216 to be easily replaced if it becomes damaged.

The shank portion 214 may have an extension length "l," and a width "sw," while the hook portion 216 may have a hook width "hw." Generally, the extension length "l" should be sufficient to allow the shank portion 214 to be pressed against an end 1002 of a bone plate 1000 (FIG. 5A) or within a bone screw hole 1004, or articulated tension device hole 1005 (FIG. 5D) of the bone plate 1000 (FIG. 5C) without interference from the hook portion 216. In one embodiment, the extension length "l" is about 7 mm and the shank width "sw" is about 2.5 mm. The hook portion 216 should be sized to allow it to be hooked under bone plate 1000 (when the instrument is used for distracting against an end of the bone plate), or to be hooked within bone screw hole 1004, or preformed hole 1005 (FIG. 5D) of the bone plate 1000 (when the instrument is used for compression) to maintain engagement of the instrument 10 with the bone plate 1000. In one embodiment, the hook width "hw" may be about 4.5 mm.

As shown in FIGS. 4B and 4C, recesses 218 and 219 may be formed in the lateral walls 226A, B of engaging arm 220B, and may be of substantially similar design so that a bone screw 1100 or guide wire 1200 may be engaged using either lateral side 226A, B of the instrument 10. Thus, when the device is used for distraction, recess 218 will engage the screw/wire 1100, 1200, whereas when the device is used for compression, recess 219 will be engaged with the screw/wire. Reference will therefore be made to recess 218 only, however, all configurations and permutations described in relation to recess 218 should be understood to apply equally to recess 219.

Figure 4D:
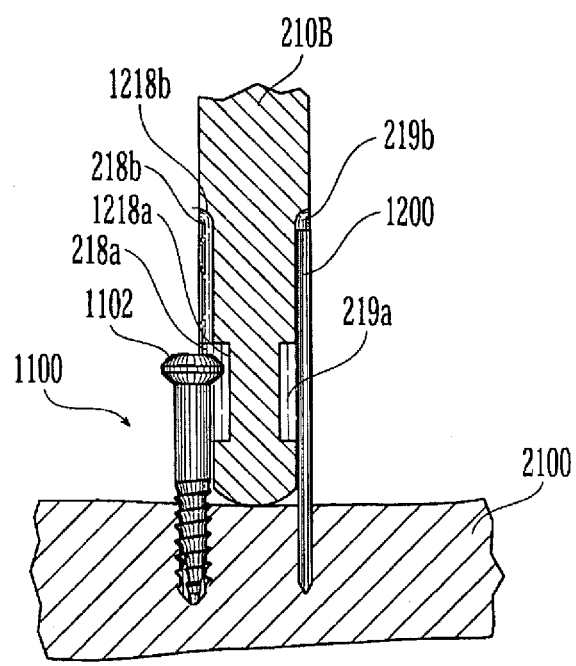
FIG. 4D is a side detail view of an engaging end of the tool of FIG. 1 engaged, for purposes of illustration, with a bone screw and a guide wire.

As can be seen in FIGS. 4A and 4B, recess 218 may be comprised of two interconnected recesses 218a, b. Recess 218a may be configured to receive the head 1102 of a bone screw 1100 (FIG. 4D), while recess 218b may be configured to receive a length of guide wire 1200 since the surgeon may use either a bone screw or guide wire to engage one of the bone segments. Recess 218a may have an engaging surface 1218a comprising a width "rw1" a length "rl1" and a maximum depth "rd1." Recess 218b likewise may have an engaging surface 1218b comprising width "rw2," a length "rl2" and a maximum depth "rd2." In one embodiment, width "rw1" may be about 8 mm, length "rl1" may be about 7 mm and depth "rd1" may be about 4 mm; width "rw2" may be about 3 mm, "rl2" may be about 26 mm and "rd2" may be about 1.75 mm.

In the illustrated embodiment, each of the recesses 218a, b, 219a, b comprise cylindrical sections having a radius of curvature substantially equal to the respective recess depth "rd1," "rd2." It is noted that although recesses 218a, b are described as having engaging surfaces 1218a, b comprising the aforementioned configurations and dimensions, the instrument 10 may be provided with one or more recesses with engaging surfaces having any appropriate configuration and size appropriate to engage an appropriate fastener for use in a distraction or compression operation. Further, recesses having engaging surface shapes other than the illustrated cylindrical configurations may also be used. Additionally, any combination of recesses having any appropriate engaging surface shape may be used. For example, the engaging surface of each recess may be flat, triangular, elliptical, etc.

Moreover, the engaging surfaces 1218a, b may be smooth, or they may have surface roughenings such as projections, coatings or other surface profilings to increase engagement between the instrument 10 and an associated bone screw 1100 or guide wire 1200.

Additionally, rather than providing a pair of individual recesses, a single recess may be provided, such as to engage only a bone screw or to engage only a guide wire. Likewise, more than two recesses may be provided to engage, for example, individual multiple bone screws or individual multiple guide wires. Further, the instrument recess or recesses may be sized and configured to engage a Shantz screw or Steinmann pin engaged with a bone segment.

Providing a tool 10 having engaging recesses 1218, 1219 allows the instrument to be inserted through a small incision in the skin, since the fastener-engaging elements do not extend laterally beyond the engaging arms 220A, 220B, an arrangement that would require additional incision length to accommodate. Thus, the present design minimizes the ultimate incision required, which in turn reduces the total time required to perform the procedure, and also reduces scarring. A smaller incision provides a more vascular injury site, and thus results in a shorter healing time for the affected bone. Limiting the incision length also reduces disruption of the periosteum, which is known to facilitate healing.

Figure 5A:
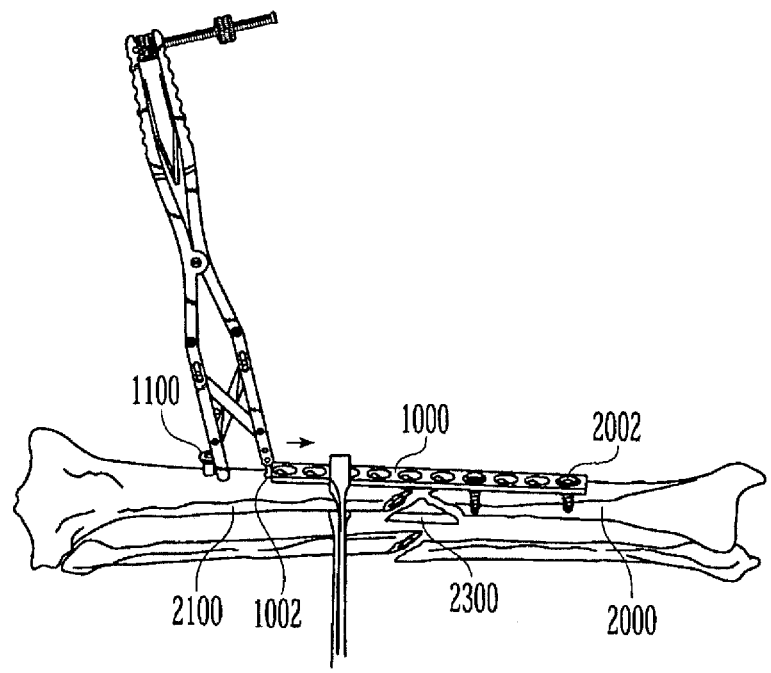
FIGS. 5A-C are perspective views of the tool of FIG. 1 engaged with a bone plate and a bone screw for distracting and then compressing a fracture.
Figure 5B:
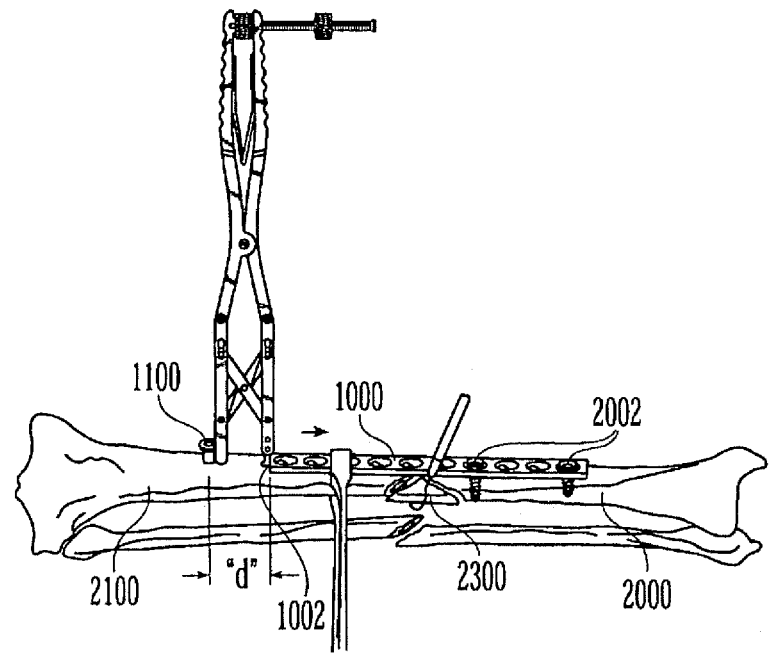
Figure 5C:
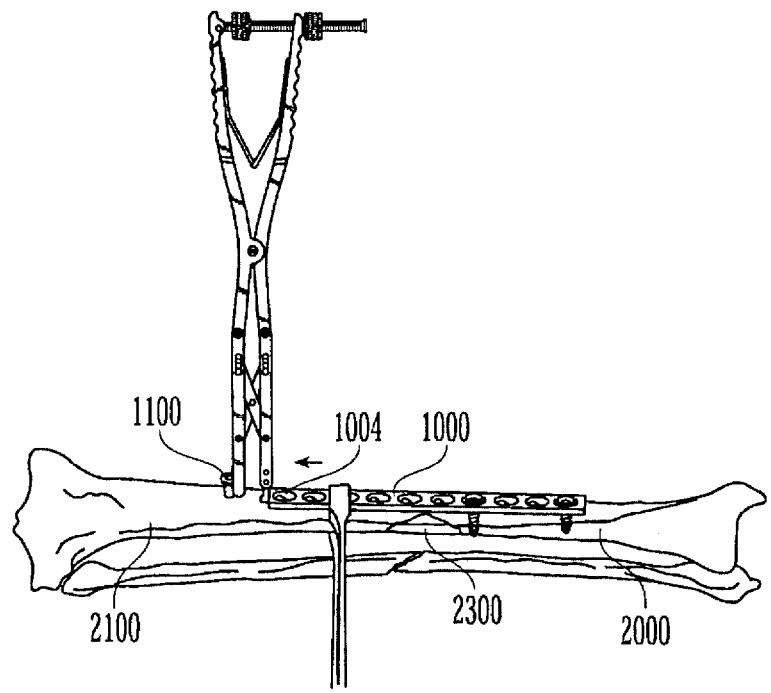
Figure 5D:
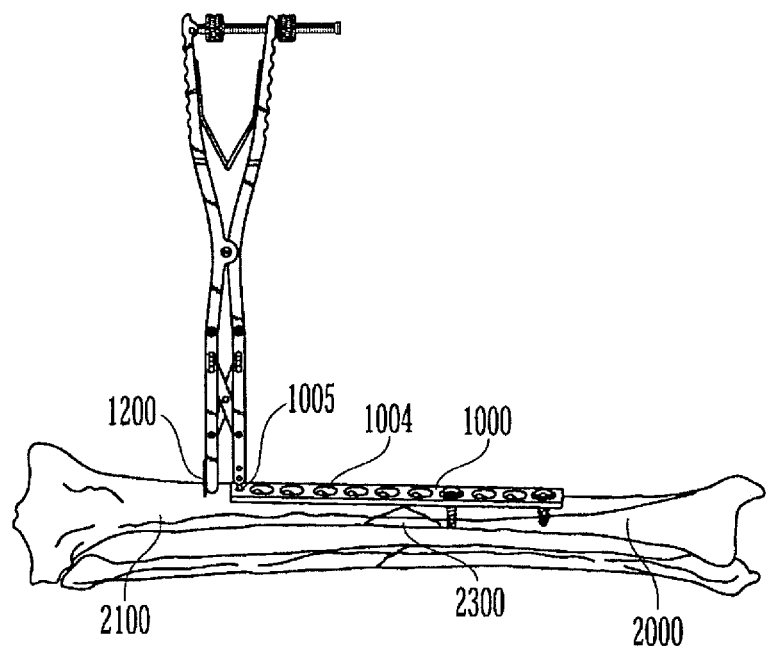
FIG. 5D is a side view of the tool of FIG. 1 engaged with a guide wire.

FIGS. 5A and 5B show the tool 10 engaged with a bone plate 1000 and a bone screw 1100 to apply a distraction force between bone segments 2000, 2100. Specifically, hook 212 engages end surface 1002 of the bone plate 1000 which is attached to bone segment 2000 while recess 218a engages the head 1102 of the bone screw 1100 which is attached to bone segment 2100. Thus applied, a squeezing force applied to the handles 110a, b may cause the engaging ends 210a, b of the instrument to separate, thus distracting the bone segments 2000, 2100. Alternatively, as shown in FIG. 5C, the tool 10 is engaged with a bone screw hole 1004 of the bone plate 1000, while the recess 219a engages the head 1102 of the bone screw 1100. In this case, a separating force applied to the handles 110a, b may cause the bone segments 2000, 2100 to be drawn together (i.e. compressed). FIG. 5D shows the instrument 10 engaged with a length of surgical guide wire 1200 that is engaged with bone segment 2100.

With reference to FIGS. 5A-5D, a method of reducing a fracture using the tool 10 of FIGS. 1-4C is also disclosed. An incision may be made in the patient's skin near the fracture, and a bone plate 1000 may be inserted through the incision so that at least a portion of the plate lies across a portion of each bone segment 2000, 2001. The plate may be fixed to one bone segment 2000 using at least one bone screw 2002. Another bone screw 1100 (or guide wire 1200) may be driven a portion of the second bone segment 2001 located a distance "d" away from the end surface 1002 of the plate 1000. The user may then insert the engaging end 200 of the tool 10 through the incision so that recess 218a engages the head portion 1002 of bone screw 1100, and the hook portion 212 engages the end surface 1002 of the plate 1000. In this position, the tool may be at or near its fully closed position (FIG. 1) so as to permit easy insertion into the incision and engagement with the fixation elements 1000, 1100. The user may then squeeze the handles 110a, b of the tool together to slightly distract the bone segments. To lock the tool 10 in this distracted position, speed nut 520 may be rotated so that it moves along threaded rod 510 and abuts handle 110a.

This slight distraction may allow the surgeon to align bone segments 2000, 2100, and may be particularly helpful when reducing a commutated fracture involving additional smaller bone segments 2300. During the distraction step, the soft tissue surrounding the fracture may act to urge the bone segments back toward their original un-fractured position (i.e. ligamentotaxis). If necessary, forceps or other tools may also be used to realign the bone segments as desired.

Once the bone segments have been re-aligned, the tool 10 may be repositioned so that the hook element 212 engages a bone screw hole 1004, or articulated tension device hole 1005 (FIG. 5D), of the plate 1000, and recess 219a engages the head 1102 of bone screw 1100 (or guide wire 1200). The user may then apply a separation force between the handles 110a, b to cause the engaging ends 210a, b to come together, thereby forcing the engaged bone fragments 2000, 2001 to be compressed together. Again, the tool 10 may be locked in position, this time by turning speed nut 530 along threaded shaft 510 until the nut 530 contacts handle 110a, thus locking the bone segments together until the bone plate can be fixed to bone segment 2100 to fix the segments together permanently. The tool 10 may then be removed from the incision and additional procedures performed if required.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. The presently disclosed embodiments are therefore to be considered in all respects as illustrative and not restrictive, the scope of the invention being indicated by the appended claims, and not limited to the foregoing description.

What is claimed is:

1. A method for manipulating bone segments, comprising:
   advancing an engaging end of a tool through an incision in a patient's skin to a target bone;
   engaging an end of a first engaging arm of the tool with a bone fastener inserted into a first bone segment via a first recess extending along one of an engaging surface and an opposing outer surface of the first engaging arm, the first recess including a first portion and a second portion interconnected with one another, the first portion configured to receive at least a portion of a guide wire and the second portion configured to receive a portion of a bone screw;
   engaging an end of second engaging arm of the tool with a bone plate fixed to a second bone segment; and
   moving the first and second bone segments relative to one another by pivoting first and second handles coupled to the first and second engaging arms, respectively, relative to one another.

2. The method of claim 1, wherein the first engaging arm further includes a second recess extending along the other of the engaging surface and the outer surface, the second recess including a first portion and a second portion, the first portion of the second recess configured to receive at least a portion of a guide wire and the second portion of the second recess configured to receive a portion of a bone screw.

3. The method of claim 1, wherein moving the first and second bone segments relative to one another includes moving the first and second handles toward one another to separate the first and second engaging arms.

4. The method of claim 1, wherein moving the first and second bone segments relative to one another includes moving the first and second handles away from one another to draw the first and second engaging arms toward one another.

5. The method of claim 1, wherein the first and second engaging arms extend substantially parallel to one another.

6. The method of claim 1, wherein engaging the end of the first engaging arm with the bone fastener includes receiving a head portion of a bone screw in the second portion of the first recess.

7. The method of claim 1, wherein engaging the end of the first engaging arm with the bone fastener includes receiving a portion of a guide wire in the first portion of the first recess.

8. The method of claim 1, wherein engaging the end of the second engaging arm with the bone plate includes engaging a hook at the end of the second engaging arm with one of an end surface of the bone plate and a bone screw hole of the bone plate.

9. The method of claim 1, further comprising locking a locking mechanism to lock the first and second engaging arms in a desired position relative to one another.

10. The method of claim 9, wherein locking the locking mechanism includes one of (a) rotating a first speed nut mounted on a threaded bolt coupled to one of the first and second handles and passing through the other of the first and second handles until the first speed nut contacts an exterior surface thereof to maintain the first and second bone segments in a desired distracted position and (b) rotating a second speed nut mounted over the threaded bolt between the first and second handles until the second speed nut contacts an interior surface of the other of the first and second handles to maintain the first and second bone segments in a desired compressed configuration.

11. The method of claim 1, wherein the first and second engaging arms are in a closed configuration when advanced to the target bone, the first and second engaging arms biased toward the closed configuration.

12. A tool for manipulating bone segments, comprising:
   first and second handles pivotably coupled to one another;
   a first engaging arm extending from a first end coupled to the first handle to a second end configured to engage a bone fastener, the second end including a first recess extending along a first recess surface thereof, the first recess surface forming a portion of one of an engaging surface and an opposing outer surface of the second end of the first engaging arm, the first recess including a first portion and a second portion interconnected with one another, the first portion configured to receive at least a portion of a guide wire and the second portion configured to receive a portion of a bone screw wherein the first portion extends partially into the first recess surface a first depth and the second portion extends partially into the first recess surface a second, smaller depth; and
   a second engaging arm extending from a first end coupled to the second handle to a second end configured to engage a bone plate, the first and second engaging arms coupled to the first and second handles, respectively, such that pivoting the first and second handles moves the first and second engaging arms toward and away from one another.

13. The tool of claim 12, wherein the first engaging arm further includes a second recess extending along a second recess surface forming part of the one of the engaging surface and the outer surface that does not include the first recess surface, the second recess including a first portion and a second portion, the first portion of the second recess configured to receive at least a portion of a guide wire and the second portion of the second recess configured to receive a portion of a bone screw.

14. The tool of claim 13, wherein the first recess is a compression recess formed on the inner surface of the first engaging arm facing the second engaging arm, and the second recess is formed on the outer surface as a distraction recess.

15. The tool of claim 12, wherein the first and second handles are coupled to the first and second engaging arms such that pivoting the first and second handles toward one another separates the first and second engaging arms and pivoting the first and second handles away from one another draws the first and second engaging arms toward one another.

16. The tool of claim 12, wherein the first and second engaging arms extend substantially parallel to one another.

17. The tool of claim 12, wherein the second end of the second engaging arm includes a hook engageable with one of an end surface of the bone plate and a bone screw hole of the bone plate.

18. The tool of claim 12, further comprising a locking mechanism to lock the first and second engaging arms in a desired position relative to one another.

19. The tool of claim 18, wherein the locking mechanism includes a threaded bolt coupled to one of the first and second handles and passing through the other of the first and second handles, a first speed nut rotatably mounted over a portion of the threaded bolt extending laterally from the other of the first and second handles and a second speed nut mounted over a portion of the threaded bolt extending between the first and second handles.

20. The tool of claim 12, wherein the first and second arms are biased toward a closed configuration via a biasing element.

21. The tool of claim 20, wherein the biasing element is a pair of leaf springs coupled to the first and second handles.

* * * * *